US012616741B2

(12) United States Patent　　(10) Patent No.: US 12,616,741 B2
Jobe et al.　　　　　　　　　　　(45) Date of Patent:　May 5, 2026

(54) THERAPEUTIC COMBINATION COMPRISING A PULMONARY SURFACTANT AND A STEROID FOR THE PROPHYLAXIS OF BPD

(71) Applicants:CHIESI FARMACEUTICI S.p.A., Parma (IT); CHILDREN'S HOSPITAL MEDICAL CENTER, Cincinnati, OH (US)

(72) Inventors: Alan Jobe, Cincinnati, OH (US); Augusto Schmidt, Cincinnati, OH (US); Noah Hillman, Saint Louis, MO (US); Matthew Kemp, Melville (AU)

(73) Assignees: CHILDREN'S HOSPITAL MEDICAL CENTER, Cincinnati, OH (US); SAINT LOUIS UNIVERSITY SCHOOL OF MEDICINE, St. Louis, MO (US); WOMEN AND INFANTS RESEARCH FOUNDATION, Subiaco (AU)

( * ) Notice: Subject to any disclaimer, the term of this patent is extended or adjusted under 35 U.S.C. 154(b) by 0 days.

(21) Appl. No.: 17/204,412

(22) Filed: Mar. 17, 2021

(65) Prior Publication Data

US 2021/0220445 A1　　Jul. 22, 2021

Related U.S. Application Data

(63) Continuation of application No. 16/384,994, filed on Apr. 16, 2019, now abandoned.

(60) Provisional application No. 62/751,830, filed on Oct. 29, 2018, provisional application No. 62/661,245, filed on Apr. 23, 2018.

(51) Int. Cl.
| | |
|---|---|
| *A61K 9/00* | (2006.01) |
| *A61K 31/573* | (2006.01) |
| *A61K 35/42* | (2015.01) |
| *A61K 38/17* | (2006.01) |
| *A61P 9/00* | (2006.01) |

(52) U.S. Cl.
CPC .......... *A61K 38/395* (2013.01); *A61K 9/0073* (2013.01); *A61K 31/573* (2013.01); *A61K 35/42* (2013.01); *A61P 9/00* (2018.01)

(58) Field of Classification Search
CPC .. A61K 38/395; A61K 31/573; A61K 9/0082; A61K 9/0073; A61K 35/42; A61P 9/00
See application file for complete search history.

(56) References Cited

U.S. PATENT DOCUMENTS

| | | | |
|---|---|---|---|
| 6,019,968 A | 2/2000 | Platz et al. | |
| 8,357,657 B2 * | 1/2013 | Giossi .................... | A61K 35/42 |
| | | | 514/15.5 |
| 10,668,110 B2 * | 6/2020 | Fabbri .................... | A61K 9/007 |
| 2002/0017295 A1 | 2/2002 | Weers et al. | |
| 2002/0037316 A1 | 3/2002 | Weers et al. | |
| 2002/0187106 A1 | 12/2002 | Weers et al. | |
| 2004/0105820 A1 | 6/2004 | Weers et al. | |
| 2005/0042175 A1 | 2/2005 | Nilsson et al. | |
| 2005/0222111 A1 | 10/2005 | Andersson et al. | |
| 2005/0229926 A1 | 10/2005 | Fink et al. | |
| 2005/0229929 A1 | 10/2005 | Ivri | |
| 2007/0225233 A1 | 9/2007 | Yeh | |
| 2009/0047358 A1 | 2/2009 | Weers et al. | |
| 2010/0119587 A1 | 5/2010 | Amighi et al. | |
| 2010/0317636 A1 | 12/2010 | Yeh | |
| 2014/0142021 A1 * | 5/2014 | Johansson ............... | A61P 11/00 |
| | | | 514/1.5 |
| 2018/0110948 A1 | 4/2018 | Dellaca et al. | |
| 2018/0177832 A1 | 6/2018 | Fabbri et al. | |

FOREIGN PATENT DOCUMENTS

| | | |
|---|---|---|
| CA | 2 643 761 A1 | 9/2007 |
| CN | 105362220 A | 3/2016 |
| EP | 1 674 085 A1 | 6/2006 |
| EP | 2 719 391 A1 | 4/2014 |
| JP | 2007-262064 A | 10/2007 |
| JP | 2015-514481 A | 5/2015 |
| RU | 2 157 222 C2 | 10/2000 |
| WO | WO 01/85136 A2 | 11/2001 |
| WO | WO 2007/005672 A2 | 1/2007 |
| WO | WO 2016/170087 A1 | 10/2016 |
| WO | WO 2018/115013 A1 | 6/2018 |

OTHER PUBLICATIONS

McEvoy "Steroids and Surfactant in Extremely Low Gestation Age Infants Dose Escalation Trial (SASSIE)", NCT02907593, ClinicalTrials. gov, first posted Sep. 20, 2016, pp. 1-9 (Year: 2016).*
McEvoy et al. "Dose-escalation trial of budesonide in surfactant for prevention of bronchopulmonary dysplasia in extremely low gestational age high-risk newborns (SASSIE)", Pediatric Research, 2020, pp. 1-8 (Year: 2020).*
Jones "Drug Criteria & Outcomes Poractant alfa (Curosurf) Formulary Evaluation", Relias Media, 2005 (Year: 2005).*
DiBlasi "Nasal Continuous Positive Airway Pressure (CPAP) for the Respiratory Care of the Newborn Infant", Respiratory Care, 2009, 1209-1235 (Year: 2009).*
Ke et al. "Efficacy of different preparations of budesonide comtress syndrome: a comparative analysis", Contemporary Chinese journal pediatrics, 2016, pp. 400-404 (Year: 2016).*
Mikolka et al. "Budesonide Added to Modified Porcine Surfactant Curosurf May Additionally Improve the Lung Functions in Meconium Aspiration Syndrome", Physiol. Res. 2013, S191-S200 (Year: 2013).*
Ricci_et_al_Pediatric_Research_2017 (Year: 2017).*
International Search Report and Written Opinion issued on Jul. 26, 2019, in PCT/EP2019/059742, 16 pages.

(Continued)

*Primary Examiner* — Catherine S Hibbert
(74) *Attorney, Agent, or Firm* — Oblon, McClelland, Maier & Neustadt, L.L.P.

(57) ABSTRACT

Administering a pulmonary surfactant and a corticosteroid in a low dose is effective for the prophylaxis of bronchopulmonary dysplasia (BPD) in preterm neonates.

17 Claims, 4 Drawing Sheets

(56) References Cited

OTHER PUBLICATIONS

Kuo, H. T. et al., "A Follow-up Study of Preterm Infants Given Budesonide Using Surfactant as a Vehicle to Prevent Chronic Lung Disease in Preterm Infants", The Journal of Pediatrics, XP026975163, vol. 156, No. 4, Apr. 1, 2010, pp. 537-541.

Yeh, T. F. et al., "Early Intratracheal Instillation of Budesonide Using Surfactant as a vehicle to Prevent Chronic Lung Disease in Preterm Infants: A Pilot Study", Pediatrics, XP009514140, vol. 121, No. 5, May 1, 2008, pp. 1310-1318.

Yeh, T. F. et al., "Early Intratracheal Instillation of Budesonide Using Surfactant as a vehicle to Prevent Chronic Lung Disease in Preterm Infants: A Pilot Study", Pediatrics, XP002792456, vol. 121, No. 5, 2008, pp. 1310-1318.

Kothe, T.B., et al., "Effects of budesonide and surfactant in preterm fetal sheep", Am. J. Physiol Lung Cell Mol. Physiol, vol. 315, Apr. 19, 2018, pp. L193-L201.

Yee et al. "Does the use of primary continuous positive airway pressure reduce the need for intubation and mechanical ventilation in infants ≤S32 weeks' gestation?", Pediatric Child Health vol. 16 No Dec. 10, 2011; pp. 633-637 (Year: 2011).

Ke et al. "Efficacy of different preparations of budesonide combined with pulmonary surfactant in the treatment of neonatal respiratory distress syndrome: a comparative analysis", Contemporary Chinese journal pediatrics, 2016, pp. 400-404 (Year: 2016).

Ricci et al. "In vitro and in vivo characterization of poractant alfa supplemented with budesonide for safe and effective intratracheal administration", Pediatric Research, 2017, pp. 1056-1063 (Year: 2017).

Russian Search Report issued Oct. 14, 2022 in Russian Patent Application No. 2020138040/04 (submitting English translation only), 3 pages.

Yeh et al., "Intratracheal Administration of Budesonide/Surfactant to Prevent Bronchopulmonary Dysplasia", American Journal of Respiratory and Critical Care Medicine, Jan. 1, 2016, vol. 193, No. 1, pp. 86-95.

Barrette et al., "Antiinflammatory Effects of Budesonide in Human Fetal Lung", American Journal of Respiratory Cell and Molecular Biology, vol. 55, No. 5, Nov. 2016, pp. 623-632.

"Steroids and Surfactant in Extremely Low Gestation Age Infants Dose Escalation Trial", ClinicalTrials.gov, retrieved from https://clinicaltrials.gov/study/NCT029075937tab=history&a=4, Oct. 17, 2017, 6 pages.

* cited by examiner

Figure 1

THERAPEUTIC COMBINATION COMPRISING A PULMONARY SURFACTANT AND A STEROID FOR THE PROPHYLAXIS OF BPD

CROSS REFERENCES TO RELATED APPLICATIONS

This application claims priority to U.S. Provisional Patent Application No. 62/661,245, filed on Apr. 23, 2018, and U.S. Provisional Patent Application No. 62/751,830, filed on Oct. 29, 2018, both of which are incorporated herein by reference in their entireties.

BACKGROUND OF THE INVENTION

Field of the Invention

The present invention relates to compositions for the prophylaxis of diseases of prematurity. The present invention also relates to methods for the prophylaxis of diseases of prematurity.

Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

The lung surfactant complex is composed primarily of lipid and contains minor amounts of various proteins. An absence of adequate levels of this complex results in malfunction of the lungs. This syndrome is called Respiratory Distress Syndrome (RDS) and it commonly affects preterm neonates.

The mainstay of the treatment of RDS is the replacement therapy with exogenous pulmonary surfactant preparations extracted from animal lungs, known as modified natural surfactants. For instance, modified natural surfactants used in the clinical practice are poractant alfa derived from porcine lung, and sold under the trademark of Curosurf®, beractant (Surfacten® or Survanta®) bovactant (Alveofact®), both derived from bovine lung, and calfactant derived from calf lung (Infasurf®).

Exogenous pulmonary surfactants are currently administered by endotracheal instillation as a suspension in a saline aqueous solution to intubated pre-term infants kept under mechanical ventilation with oxygen.

Although said therapy has greatly increased postnatal survival, children that survive RDS have a high risk of developing broncho-pulmonary dysplasia (BPD), a common and serious complication of prematurity, associated with significant mortality, morbidity and healthcare resource utilization. Despite advances in both prenatal and neonatal care the incidence of the condition continues to rise. The management of BPD and its related problems remains a major challenge for neonatologists and pediatricians. Multiple interventions have been proposed to prevent and treat BPD but many are still not evidence based. Current treatments appear to have reduced the severity of BPD but have had little effect on its incidence. BPD is an evolving process of lung injury and its pathophysiology varies at different stages of the disease. Its management therefore is unlikely to be in the form of a single intervention but rather a combined approach with different strategies used to target different factors and/or stages of the disease.

For this reason, it is useful to categorize intervention for BPD at three subsequent stages when designing an overall management plan. These are: i) prevention of BDP; ii) treatment of evolving BPD; and iii) treatment of established BPD (see Bowen P et al Pediatrics and Child Health 2013, 24:1, 27-31, which is incorporated herein by reference in its entirety).

The prevention of BPD in neonates affected by RDS has been managed by systemic administration of a corticosteroid, antenatal or within few hours postnatal. However, the effectiveness of postnatal corticosteroid administration is offset by possible adverse systemic effects, e.g., hypertension, hyperglycemia, gastrointestinal complications, and neurodevelopmental disability.

As an alternative to systemic administration, delivery of corticosteroid by inhalation or intracheal instillation has been proposed for the prophylaxis of BDP.

For example, US 2010/0317636, which is incorporated herein by reference in its entirety, discloses a method for the prophylaxis of BPD in an infant suffering from respiratory distress syndrome by administering to the infant a combination of a corticosteroid having a high local to systemic anti-inflammatory activity and a lung surfactant.

Yeh et al (Pediatrics 2008, 121 (5), e1310-e1318, which is incorporated herein by reference in its entirety) proposed the intratracheal instillation of budesonide using the pulmonary surfactant Survanta® as a carrier, while Dani et al (Pediatr Pulmonol 2009, 44, 1159-1167, which is incorporated herein by reference in its entirety) have proposed the intratracheal instillation of beclometasone dipropionate in combination with Cursourf®.

However, through these approaches as well, a large population of preterm neonates would be exposed to corticosteroids, many without benefit if otherwise they would not develop BPD (see Bancalari E Am J Respir Crit Care Med 2016, 193:1, 12, which is incorporated herein by reference in its entirety).

Postnatal corticosteroids could find their place in therapy in the prevention of BPD as in this way they will be administered to patients in need thereof.

However, due to the observed side effects or to the lack of clear sign of efficacy, the systemic postnatal administration of dexamethasone and hydrocortisone is not currently recommended routinely.

In view of the above considerations, there is still a need to develop a more compliant corticosteroid-based medicament for the prophylaxis of BPD in premature neonates, mitigating the risk of adverse side-effects.

Furthermore, it would be advantageous to provide a medicament that may be administered locally either by inhalation or intra-tracheal instillation.

SUMMARY OF THE INVENTION

Accordingly, it is one object of the present invention to provide novel compositions for the prophylaxis of diseases of prematurity.

It is another object of the present invention to provide novel methods for the prophylaxis of diseases of prematurity.

These and other objects, which will become apparent during the following detailed description, have been achieved by the inventors' discovery that administration of a pulmonary surfactant in combination with budesonide is useful for the prevention of bronchopulmonary dysplasia (BPD) in preterm neonates.

Thus, the present invention provides the use of a pulmonary surfactant in combination with a steroid for the prophylaxis of broncho-pulmonary dysplasia in preterm neonates.

Accordingly, in one embodiment, the present invention is directed to a pulmonary surfactant in combination with budesonide at a dose of about 0.01 to about 0.1 mg/kg of body weight for use for the prophylaxis of bronchopulmonary dysplasia (BPD) in preterm neonates.

Advantageously, said combination is administered from the birth (within the $1^{st}$ of life) to the $4^{th}$ day of life.

The present invention also relates to a pulmonary surfactant in combination with budesonide at a dose of about 0.01 to about 0.1 mg/kg of body weight for use for the treatment of severe chronic pulmonary insufficiency of prematurity in preterm neonates.

The present invention is also directed to the use of a pulmonary surfactant in combination with budesonide at a dose of about 0.01 to about 0.1 mg/kg of body weight in the manufacture of a medicament for the prophylaxis of bronchopulmonary dysplasia (BPD) in preterm neonates.

Advantageously, said combination is administered from the birth (within the $1^{st}$ of life) to the $4^{th}$ day of life.

The present invention also relates to the use of a pulmonary surfactant in combination with budesonide at a dose of about 0.01 to about 0.1 mg/kg of body weight in the manufacture of a medicament for the treatment of severe chronic pulmonary insufficiency of prematurity in preterm neonates.

The medicament of the present invention could be administered simultaneously, sequentially or separately, preferably for simultaneous administration as fixed combination.

In a particular embodiment, said medicament is in the form of pharmaceutical composition for inhalation or intratracheal administration comprising said fixed combination.

In another embodiment, the present invention is directed to a method for the prophylaxis of bronchopulmonary dysplasia or the treatment of severe chronic pulmonary insufficiency of prematurity, comprising administering to a preterm neonate in need of such prophylaxis a pulmonary surfactant in combination with budesonide at a dose of about 0.01 to about 0.1 mg/kg of body weight, wherein said combination is administered from the birth (within the $1^{st}$ day of life) to the $4^{th}$ day of life.

In a further embodiment, the invention is directed to a method of improving lung function in a pre-term neonate, comprising the step of administering the composition of the invention.

In an even further embodiment, the invention is directed to a method of reducing lung inflammation in a pre-term neonate treated with mechanical ventilation, comprising the step of administering the composition of the invention to said pre-term neonate, wherein said administration occurs during, before, or after said mechanical ventilation.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the results of Example 5.

DETAILED DESCRIPTION OF THE PREFERRED EMBODIMENTS

Figure 2:
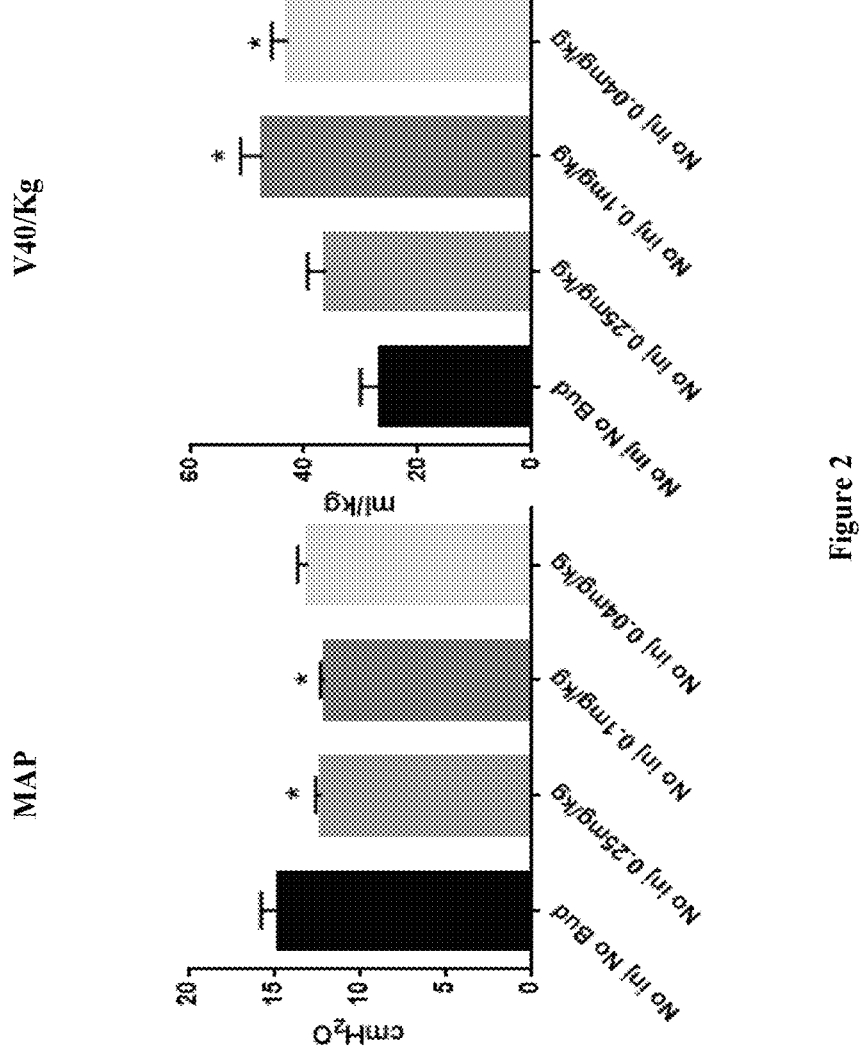
FIG. 2 shows the results of the mean airway pressure (MAP) and the volume at 40 cmH$_2$O (V40/kg) of Example 6.

The term "bronchopulmonary dysplasia (BPD)" refers to a chronic pulmonary disorder, also known as chronic lung disease (CLD), which is the consequence of unresolved or abnormally repaired lung damage. BDP may also be referred to severe chronic pulmonary insufficiency of prematurity.

BPD typically occurs in very low birth weight (VLBW) infants who sustain lung damage as a result of oxygen toxicity and barotrauma from mechanical ventilation early in life. The definition and classification of BPD have changed since its original description by Northway et al. in 1967. The National Institute of Child Health and Human Development (NICHD) defined BPD in a consensus statement in 2001. This definition uses supplemental oxygen requirement for 28 days and then identifies 3 grades of severity, dependent on the respiratory support required at either 36 week postmenstrual age (PMA) or at discharge for those born at <32 weeks gestation or at 56 days of life or discharge for those born at >32 weeks gestation.

In 2001 Jobe A et al (*Am J Respir Crit Care Med;* 163 (7) 1723-1729, which is incorporated herein by reference in its entirety) proposed a new definition including specific criteria for 'mild,' 'moderate' and 'severe' BPD.

Mild BDP is defined as the disease requiring supplemental oxygen for ≥28 days and on room air at 36 weeks PMA or at discharge (for infants <32 weeks at birth) or at 56 days or at discharge (for infants ≥32 weeks at birth).

Moderate BDP is defined as the disease requiring supplemental oxygen for ≥28 days and a need for supplemental oxygen <30% at 36 weeks PMA/discharge (for <32 weeks) or at 56 days/discharge (for infants ≥32 weeks).

Severe BPD is defined as the disease requiring supplemental oxygen for ≥28 days and a need for ≥30% oxygen or on nasal CPAP or mechanical ventilation at 36 weeks PMA/discharge (<32 weeks) or at 56 days/discharge (≥32 weeks).

The term "evolving BPD", sometimes known as early BPD, refers to the initial phase of the chronic process leading to established BDP and indicates the disease characterized by oxygen and/or ventilator-dependency from $7^{th}$ to $14^{th}$ day of life (Walsh M C et al Pediatrics 2006, 117, S52-S56, which is incorporated herein by reference in its entirety). Recently evolving BPD has also been referred to as chronic pulmonary insufficiency of prematurity (see Steinhorn R et al J Peds 2017, 8, 15-21, which is incorporated herein by reference in its entirety).

The term "modified natural surfactant" refers to a lipid extract of minced mammalian lung. Due to the lipid extraction process used in the manufacture process, the hydrophilic proteins SP-A and SP-D are lost. These preparations have variable amounts of two hydrophobic, surfactant-associated proteins SP-B and SP-C and, depending on the method of extraction, may contain non-surfactant lipids, proteins or other components.

The term "poractant alfa" refers to a modified natural surfactant extracted from porcine lungs substantially consisting of polar lipids, mainly phospholipids and the proteins, SP-B and SP-C. Poractant alfa is available under the trademark Curosurf®.

The term "artificial" pulmonary surfactants refers to simply mixtures of synthetic compounds, primarily phospholipids and other lipids that are formulated to mimic the lipid composition and behavior of natural pulmonary surfactant. They are devoid of pulmonary surfactant proteins.

The term "reconstituted" pulmonary surfactants" refers to artificial pulmonary surfactants to which have been added pulmonary surfactant proteins/peptides isolated from animals or proteins/peptides manufactured through recombinant technology such as those described in WO 95/32992, which is incorporated herein by reference in its entirety, or synthetic pulmonary surfactant protein analogues such as those described in WO 89/06657, WO 92/22315, and WO 00/47623, all of which are incorporated herein by reference in their entireties.

The term "non-invasive ventilation (NIV) procedure" defines a ventilation modality that supports breathing without the need for intubation such as nasal Continuous Positive Airway Pressure (nasal CPAP). Other non-invasive ventilation procedures are nasal intermittent positive-pressure ventilation (NIPPV), High Flow Nasal Cannula (HFNC), and bi-level positive airway pressure (BiPAP).

The term "respiratory support" includes any intervention that treats respiratory illness including, for example, the administration of supplemental oxygen, mechanical ventilation, and nasal CPAP.

The term "treatment" refers to the use for curing, symptom-alleviating, symptom-reducing of the disease or condition, e.g., BPD in the patient.

The term "prophylaxis" refers to the slowing of the progression, delaying the onset, and/or reducing the risk of contracting the disease or condition, e.g., BPD, in the patient.

The term "pre-term neonates", or preterm infants, includes extremely low birth weight (ELBW), very-low-birth-weight (VLBW), and low-birth weight (LBW) neonates of 24 to 35 weeks gestational age.

The term "fixed combination" means a combination wherein the active substances are in a fixed quantitative ratio.

"Pharmaceutically acceptable" is a term used herein that refers to a medium that does not produce an allergic or similar untoward reaction when administered to an infant.

"Surfactant activity" for a surfactant preparation is defined as the ability to lower the surface tension.

The in vitro efficacy of exogenous surfactant preparations is commonly tested by measuring their capability of lowering the surface tension using suitable apparatus such as Wilhelmy Balance, Pulsating Bubble Surfactometer, Captive Bubble Surfactometer and Capillary Surfactometer.

The in vivo efficacy of exogenous surfactant preparations is tested by measuring lung mechanics in pre-term animal models according to known methods.

In the context of the present description, the term "synergistic" means that the activity of the pulmonary surfactant plus that of budesonide is more than would be expected by that of the surfactant or the budesonide alone.

With the term "biosimilar of poractant alfa," it is meant a modified natural pulmonary surfactant which has the same safety profile, it is therapeutically equivalent, it has a similarity in the quali-quantitative composition of at least 80% (in particular regarding phospholipid and surfactant proteins SP-B and SP-C) and it has a viscosity equal to or less than 15 mPas (cP) at room temperature when it is suspended in an aqueous solution at a concentration of 80/mg/ml. The viscosity can be determined according to methods known in the art.

The present invention is based in part on the unexpected finding that budesonide at a dose of about 0.01 mg/kg to about 0.1 mg/kg of body weight could be combined with a pulmonary surfactant such as poractant alfa to prevent bronchopulmonary dysplasia (BPD) without altering the surface activity of the surfactant.

The advantages of combining a pulmonary surfactant with the claimed dose of budesonide will be apparent from the following findings.

It has indeed surprisingly been found, in a study in a preterm rabbit model exposed to hyperoxia to mimic BPD, that a pulmonary surfactant such as poractant alfa in combination with a lower dose of budesonide, in comparison to the dose used for instance in Yeh et al, 2008, gives rise to a pulmonary compliance substantially equivalent. Since budesonide is a highly lipophilic corticosteroid, this might favor its mucosal absorption and uptake across phospholipid cell membranes with a negligible systemic absorption, making the combination safe for therapeutic use in preterm neonates.

Furthermore, in a study in a newborn lamb model, animals treated with poractant alfa in combination with 0.04 and 0.1 mg/kg budesonide showed a higher volume at 40 cm $H_2O$ than the ones receiving the surfactant on combination with the budesonide dose used in Yeh et al, 2008.

Due to potential age-variability in ADME properties of budesonide, it would have not been possible to predict that lower dose could still be effective.

The volume at 40 com $H_2O$ is in turn a marker of lung injury, as protein released into the lung or inflammation will cause edema and deactivate the surfactant, both favoring the occurrence of BPD.

On the other hand, the pulmonary surfactant may favor the spreading of the corticosteroid by the Marangoni effect, favoring its distribution and hence the reaching of all the interested pulmonary area.

Any pulmonary surfactant currently in use, or hereafter developed for use in respiratory distress system and other pulmonary conditions could be suitable for use in the present invention. These include modified natural, artificial and reconstituted pulmonary surfactants.

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf™, Chiesi Farmaceutici SpA, Parma, Italy), and beractant (Survanta™, Abbott Laboratories, Inc., Abbott Park, 111).

Examples of reconstituted surfactants include, but are not limited to, the compositions disclosed in EP 2 152 288, WO 2008/011559, WO 2013/120058, all of which are incorporated herein by reference in their entireties, the products lucinactant (Surfaxin™, Windtree-Discovery Laboratories Inc., Warrington, Pa.) and the product having the composition disclosed in Table 2 of Example 2 of WO 2010/139442, which is incorporated herein by reference in its entirety, i.e.

1.5% of SP-C33(leu) acetate;
0.2% of Mini-B(leu) acetate; and
DPPC:POPG in a 50:50 weight ratio.

Said reconstituted surfactant is quoted hereinafter as CGF 5633.

The pulmonary surfactant selected for use in the medicament of the present invention can be the same as, or different from, the pulmonary surfactant utilized for RDS. In a preferred embodiment, the same pulmonary surfactant is used.

In a preferred embodiment, the pulmonary surfactant is a modified natural pulmonary surfactant.

More preferably, the pulmonary surfactant is poractant alfa (Curosurf™) as it is endowed with very low viscosity, and hence it can be administered at high concentrations using a small volume of aqueous carrier.

In another embodiment, the pulmonary surfactant is a reconstituted surfactant having the composition disclosed in Table 2 of Example 2 of WO 2010/139442, which is incorporated herein by reference in its entirety.

The dose of the pulmonary surfactant to be administered will vary with the weight and gestational age of the preterm neonate, as well as with the severity of the neonate condition. Those of skill in the relevant art will be readily able to determine these factors and to adjust the dosage accordingly.

Advantageously, the dose of the pulmonary surfactant could be of about 100 to about 200 mg/kg of body weight.

In a preferred embodiment of the present invention, poractant alfa at a dose of about 100 to about 200 mg/kg of body weight could be used.

In a preferred embodiment, the dose could be of about 100 mg/kg of body weight, while in another preferred embodiment, the dose could be of about 200 mg/kg of body weight.

Advantageously, the dose of budesonide is about 0.01 to about 0.1 mg/kg of body weight. The lower limit of the dose of budesonide may be about 0.02 mg/kg of body weight, about 0.03 mg/kg of body weight, about 0.04 mg·kg of body weight, or about 0.05 mg/kg of body weight. The upper limit of the dose of budesonide may be about 0.09 mg/kg of body weight, about 0.08 mg/kg of body weight, or about 0.07 mg/kg of body weight.

For the prophylaxis of BPD the pulmonary surfactant and budesonide are administered to the preterm neonate at any time between: (a) a time as close as practicable to birth or the beginning of life to (b) any time during the fourth day of life. Within the above interval of time, the administration could be continued for a period of time deemed by a physician or other medical practitioner as appropriate to achieve the desired effect.

In another embodiment, the pulmonary surfactant and budesonide are administered to the preterm neonate at any time during the first three days of life. In another embodiment, the pulmonary surfactant and budesonide are administered to the preterm neonate at any time during the first two days of life. In another embodiment, the pulmonary surfactant and budesonide are administered to the preterm neonate at any time during the first day of life. In another embodiment, the pulmonary surfactant and budesonide are administered to the preterm neonate at any time during the first 8 hours of life. In another embodiment, the pulmonary surfactant and budesonide are administered to the preterm neonate at any time during the first four hours of life.

The frequency of administration will vary with the size and gestational age of the preterm neonate, as well as with the severity of the neonate condition and the route of administration. Those of skill in the relevant art will be readily able to determine it. For instance, the medicament of the invention could be administered once or twice.

For the prophylaxis of BPD, the pulmonary surfactant and budesonide are administered to a preterm neonate of a gestational age of 26 to 35 weeks, preferably a gestational age of 28 to 32 weeks.

Preferably, the combination of the invention is administered to pre-term neonates kept under non-invasive ventilation procedures, more preferably kept under nasal CPAP, even more preferably with a nasal device, at a pressure of from 1 to 12 cm water.

The active substances of the combination of pulmonary surfactant and budesonide at the claimed doses may be administered sequentially, separately or together. Advantageously, when the two active substances are administered together, they are administered as a fixed combination.

Therefore, the present invention also provides the use of the combination of the invention as a fixed combination in the manufacture of a medicament for preventing BPD. The medicament may be in form of pharmaceutical composition.

Said formulations may be administered in the form of a solution, dispersion, suspension or dry powder. Preferably, said compositions comprise the claimed combination suspended in a suitable physiologically tolerable solvent.

More preferably, the formulation comprises an aqueous solution, preferably sterile, which may also comprise pH buffering agents and other pharmaceutically acceptable excipients such as polysorbate 20, polysorbate 80 or sorbitan monolaurate as wetting agents and sodium chloride as isotonicity agent.

The formulations may be distributed in unit-dose or multi-dose containers, for example sealed ampoules and vials, or may be stored in a frozen or freeze-dried (lyophilized) condition requiring only the addition of sterile liquid carrier immediately prior to use.

Preferably, the formulation is supplied as sterile suspension in a buffered physiological saline (0.9% w/v sodium chloride) aqueous solution in single-use vials.

The administration of the claimed formulation may be carried out according to known methods, e.g. by endotracheal instillation, by spray administration, or nebulization by jet ultrasonic, or mesh-vibrating nebulisers commonly available on the market.

When the formulation is administered by endotracheal instillation, depending on the severity of the respiratory distress syndrome, different methods can be appropriate. For example, the claimed formulation may be administered through the endotracheal tube to pre-terns neonates kept under mechanical ventilation.

Alternatively, the formulation may be administered by the use of a thin catheter placed in the trachea and the neonate respiration supported through specially designed nasal devices such as masks, prongs or tubes according to methodology known as nasal Continuous Positive Airway Pressure (nCPAP), according to the procedure described in. WO 2008/148469, which is incorporated herein by reference in its entirety.

The latter approach would be only possible with an exogenous surfactant such as poractant alfa having a low viscosity, as a high viscosity would make the passage of the surfactant through the thin catheter more difficult.

The volume of the aqueous solution in which the two combined active substances are suspended will depend on the desired concentration.

Advantageously, the volume of the formulation should be not more than about 5.0 ml, preferably from about 4.5 to about 2.0 ml, more preferably about 3.5 to about 2.5 ml.

In other embodiments, when the pulmonary surfactant and budesonide are administered separately, the individual active substances could be formulated separately. In this case, the two individual active substances do not unconditionally have to be taken at the same time.

In the case of such a separate administration, the formulation of the two individual active substances can be packed at the same time in a suitable container mean. Such separate packaging of the components in a suitable container mean is also described as a kit.

Therefore, the present invention is also directed to a kit for the prophylaxis of broncho-pulmonary dysplasia, said kit comprising: a) a pulmonary surfactant at a dose of about 100 to about 200 mg/kg and a pharmaceutically acceptable carrier or diluent in a first unit dosage form; b) budesonide at a dose of about 0.01 to about 0.1 mg/kg of body weight and a pharmaceutically acceptable carrier or diluent in a second unit dosage form; and c) container means for containing said first and second dosage forms.

Any form of mild, moderate, severe BDP potentially affecting the premature neonate could be prevented by means of the combination of the invention.

The preterm neonate requiring the medicament of the invention may or may not exhibit respiratory distress syndrome (RDS). In one embodiment, the administration of the medicament of the invention is initiated in a neonate exhibiting RDS, following treatment of such syndrome with pulmonary surfactant or by another means (e.g., ventilation) or a combination thereof.

In certain embodiments, neonates to be treated with the medicament of the present invention require respiratory support but do not necessarily exhibit respiratory distress syndrome. These infants either have not been diagnosed with RDS or have not been treated with pulmonary surfactants for RDS.

All pre-term neonates could be eligible for the administration of the medicament of the present invention including extremely-low-birth weight (ELBW), very-low-birth weight (VLBW), and low-birth weight (LBW) neonates of 24 to 35 weeks gestational age. Preferably, the medicament is administered to VLBW neonates with severe RDS who will have a higher incidence of BPD.

In general terms, since management of BPD is unlikely to be in the form of a single intervention but rather a combined approach, the physician shall evaluate whether preterm neonates also require concomitant respiratory support and/or other suitable drugs such as vitamin A and antibiotics.

In view of the dosages of the pulmonary surfactant and budesonide and the volume of the formulation to be administered, discussed above, and the typical weight of the preterm neonate receiving the administration, the solution or suspension formulation will typically contain budesonide in a concentration of about 0.005 to about 0.05 mg/ml, preferably about 0.01 to about 0.05 mg/ml, and the pulmonary surfactant in a concentration of about 20 to about 100 mg/ml, preferably about 40 to about 80 mg/ml.

Other features of the invention will become apparent in the course of the following descriptions of exemplary embodiments which are given for illustration of the invention and are not intended to be limiting thereof.

EXAMPLES

Example 1. In Vitro Evaluation of the Surface Activity of Poractant Alfa in the Presence of Budesonide by Capillary Surfactometer The surface activity of poractant alfa (in the presence of budesonide, 2 ml, 1.0 mg) was evaluated in comparison to poractant alfa alone by a capillary surfactometer commercially available from Calmia Medical, Inc., USA.

Two samples were prepared: one from a vial of poractant alfa (1.5 ml, 80 mg/ml) by diluting with saline to a concentration 1 mg/ml in phospholipids, and the other from a vial of poractant alfa (1.5 ml, 80 mg/ml) mixed with a vial of budesonide (2 ml, 1.0 mg) and diluted with saline to the same concentration (1 mg/ml phospholipids). A 0.5 ml sample of both solutions was then assessed in the Capillary Surfactometer.

The principle of the capillary surfactometer was to simulate terminal human airways. The sample was introduced into the narrow section of a glass capillary, where the inner diameter is 0.25 mm, similar to that of a terminal human airway. At one end the capillary was connected to a bellows and a pressure transducer. When the bellows was slowly compressed, pressure is raised and recorded. The increasing pressure caused the sample to be extruded from the narrow section of the capillary. As air gets through, pressure was abruptly lowered. If the sample contained well-functioning pulmonary surfactant the sample liquid did not return to the narrow section. The steady airflow obtained by the continuous compression of the bellows met no resistance and the pressure recorded was zero. If on the other hand the sample did not contain a well-functioning pulmonary surfactant, the sample liquid returned repeatedly.

The behavior of poractant alfa in the presence of budesonide turned out to be statistically indistinguishable from that of poractant alfa alone, indicating that budesonide does not affect the surface activity of the surfactant.

Example 2. Formulation in Form of an Aqueous Suspension According to the Invention

| Ingredients | Quantity For pharmaceutical unit |
| --- | --- |
| Poractant alfa | 160 mg |
| micronised budesonide | 0.1 mg |
| Polysorbate (Tween) 20 | 2.0 mg |
| Sorbitan monolaurate | 0.4 mg |
| Sodium chloride | 18 mg |
| Water for injection q. s. for | 2.0 ml |

Example 3. Formulation in Form of an Aqueous Suspension According to the Invention

| Ingredients | Quantity For pharmaceutical unit |
| --- | --- |
| Poractant alfa | 160 mg |
| micronised budesonide | 0.04 mg |
| Polysorbate (Tween) 20 | 2.0 mg |
| Sorbitan monolaurate | 0.4 mg |

Example 4. Formulation in Form of an Aqueous Suspension According to the Invention

| Ingredients | Quantity For pharmaceutical unit |
| --- | --- |
| CHF 5633 | 160 mg |
| micronised budesonide | 0.04 mg |

-continued

| Ingredients | Quantity For pharmaceutical unit |
| --- | --- |
| Polysorbate (Tween) 20 | 2.0 mg |
| Sorbitan monolaurate | 0.4 mg |

Example 5. In Vivo Effect in a Rabbit Model

The bronchopulmonary dysplasia (BPD) preterm rabbit model exposed to hyperoxia was employed in this experiment. This model has been described in detail elsewhere (see Richter J, Toelen J, Vanoirbeek J, Kakigano A, Dekoninck P, Verbeken E, et al. (2014) Functional assessment of hyperoxia-induced lung injury after preterm birth in the rabbit. Am J Physiol Lung Cell Mol Physiol 306: L277-283; Jimenez J, Richter J, Nagatomo T, Salaets T, Quarck R, Wagennar A, Wang H, Vanoirbeek J, Deprest J, Toelen J (2016) Progressive vascular functional and structural damage in a bronchopulmonary dysplasia model in preterm rabbits exposed to hyperoxia. Int J Mol Sci 17: E1776; and Salaets T, Richter J, Brady P, Jimenez J, Nagatomo, T, Deprest J, Toelen J (2015). Transcriptome analysis of the preterm rabbit lung after seven days of hyperoxic exposure. PLOS One 10: e0136569, all of which are incorporated herein by reference in their entireties). Briefly, preterm rabbits were delivered through a cesarean section at 28 days (early saccular lung developmental phase) of gestation (term=31 days). Immediately after delivery, the pups were placed in an incubator (32° C.) and randomly divided into three groups with 5-6 animals/group (see below). The preterm rabbits were kept in hyperoxia (95% of oxygen) for four days, fed twice daily with a milk formula via an orogastric tube and received prophylactic antibiotics and vitamin K. On day 3, each animal received a single intra-tracheal injection of surfactant alone 100 mg/kg of body weight (group 1), or surfactant 100 mg/kg plus budesonide 0.05 mg/kg of body weight (group 2), or surfactant 100 mg/kg plus budesonide 0.25 mg/kg of body weight (group 3). The dose of 0.25 mg/kg is reported as optimal in Yeh et al, 2008.

After 24 hours, at day 4 after birth, the preterm rabbits were deeply anesthetized, a cannula was placed in the trachea of each animal and invasive lung function testing was performed using the Flexivent system (FlexiVent 5.2; SCIREQ) as previously described ((see Richter J, Toelen J, Vanoirbeek J, Kakigano A, Dekoninck P, Verbeken E, et al. (2014) Functional assessment of hyperoxia-induced lung injury after preterm birth in the rabbit. Am J Physiol Lung Cell Mol Physiol 306: L277-283; Jimenez J, Richter J, Nagatomo T, Salaets T, Quarck R, Wagennar A, Wang H, Vanoirbeek J, Deprest J, Toelen J (2016) Progressive vascular functional and structural damage in a bronchopulmonary dysplasia model in preterm rabbits exposed to hyperoxia. Int J Mol Sci 17: E1776; and Salaets T, Richter J, Brady P, Jimenez J, Nagatomo, T, Deprest J, Toelen J (2015). Transcriptome analysis of the preterm rabbit lung after seven days of hyperoxic exposure. PLOS One 10: e0136569, all of which are incorporated herein by reference in their entireties). The pressure volume perturbation (PVr-V) was used to measure static compliance (elastic recoil pressure of the lung at a given lung volume). Three measures were obtained per pup (coefficient of determination >0.95). The mean value of the three measures was normalized by body weight and used in the analysis. After this, pups were euthanized.

Figure 1:
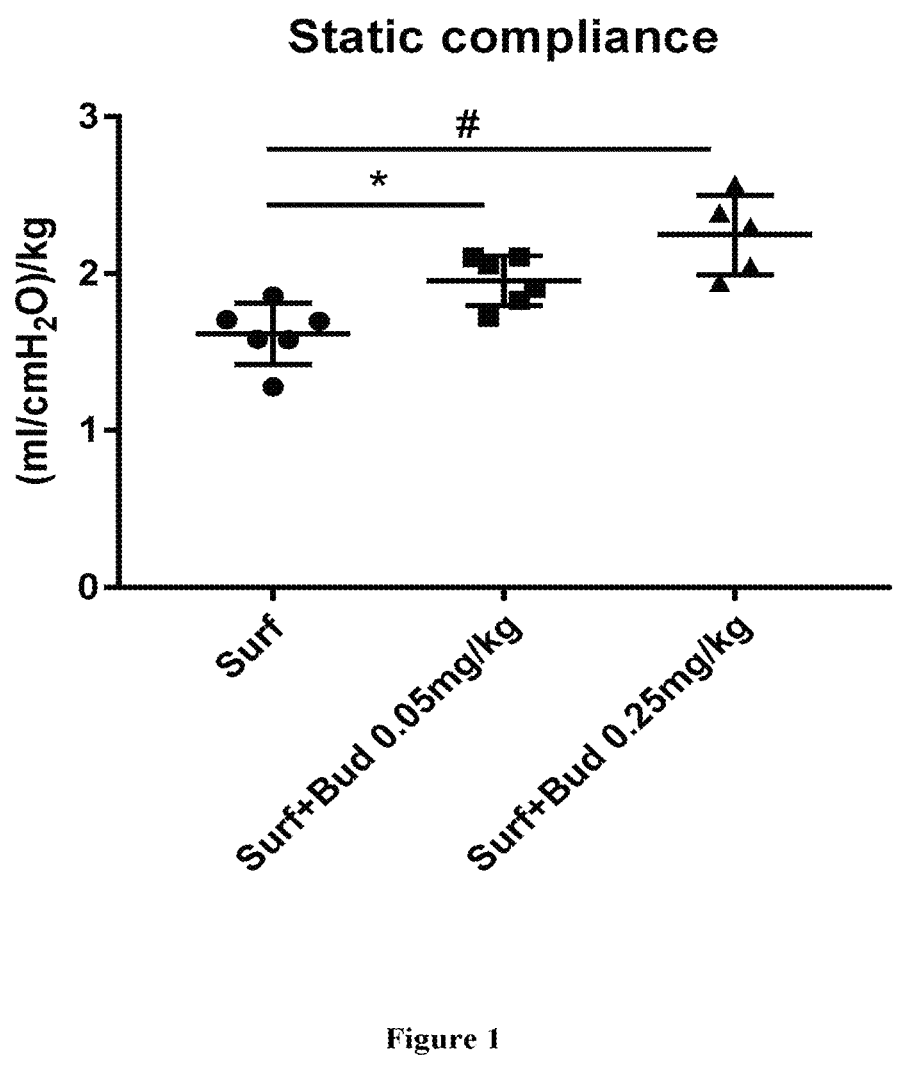

After 4 days of exposure to hyperoxia and 24 hours after surfactant±budesonide intra-tracheal administration, animals were deeply anesthetized. Pulmonary static compliance was measured as described in methods. The results are shown in Table 1 and FIG. 1. Means±standard deviations are plotted in FIG. 1 and indicated in Table 1 (black circles received surfactant alone 100 mg/kg; black squares received surfactant 100 mg/kg plus budesonide 0.05 mg/kg; black triangles received surfactant 100 mg/kg plus budesonide 0.25 mg/kg). Data were analyzed with one-way ANOVA and Turkey's multiple comparisons test (#p=0.0004; *p=0.03, when comparing surfactant alone group with surfactant plus budesonide groups).

TABLE 1

| | Surfactant | Surfactant + Budesonide 0.05 mg/kg | Surfactant + Budesonide 0.25 mg/kg |
| --- | --- | --- | --- |
| Static compliance $(mL/cmH_2O)/kg$ | 1.62 ± 0.19 | 1.95 ± 0.16 * | 2.25 ± 0.25 # |

As it can be appreciated from Table 1, a substantially similar effect is achieved in comparison to the dose of budesonide used in Yeh et al, 2008.

Example 6. In Vivo Effect in a Lamb Model

The aim of this study was to use the lamb model to test the hypothesis that low doses of budesonide in poractant alfa are comparably effective for improving physiology and indicators of inflammation with less systemic effects.
Experimental Procedure Ewes were date mated with pregnancy verification at about 50 days' gestation. The ewes were not be manipulated prior to operative delivery of the fetus. The ewe was sedated with IV ketamine and given spinal anesthesia. The fetal head and neck was exposed and the fetus was given IM-10 mg/kg ketamine estimated fetal weight as supplemental sedation and lidocaine infiltration of the skin over the trachea. A 4.5 mm endotracheal tube was secured in the trachea, followed by aspiration of fetal lung fluid through ET tube with 50 ml syringe and gentle suction. The lamb was delivered, superficially dried, weighed and placed on mechanical ventilation with initial period of body positioning to assist with even distribution of the surfactant/budesonide in the lungs. Newborn lambs were randomized to 2 treatments:

Curosurf at 200 mg/kg (2.5 ml/kg)+budesonide at 0.1 mg/kg (0.5 ml/kg)

Curosurf at 200 mg/kg (2.5 ml/kg)+budesonide at 0.04 mg/kg (0.5 ml/kg)

For comparative purposes, Curosurf at 200 mg/kg+budesonide at 0.25 mg/kg was used.

The surfactant (7.5 ml based on estimated weight of 3 kg) was drawn up into a 10 ml syringe, followed by the budesonide or saline for a total 9 ml. The mixture was rotated manually multiple times to allow components to mix. The combination of surfactant and treatment drug was rotated again prior to administration. The lambs were treated by tracheal instillation with chest positioning just prior to the initiation of mechanical ventilation to help distribute the surfactant.

Each lamb was placed on an infant warming bed. Ventilation was with a Fabian infant ventilator set to deliver 40% heated and humidified oxygen with an initial peak inspiratory pressure of 30 cmH$_2$O, a positive end expiratory pressure of 5 cmH$_2$O, a rate of 50 breaths/min, and an inspiratory time of 0.5 sec. The tidal volume was controlled by adjusting peak respiratory pressure to not exceed 8 ml/kg unless the PCO$_2$ is greater than 50 mmHg. The lambs received ketamine and were fully sedated and did not spontaneously breathe. Blood gas measurements were at 15 and 30 min and at 1 hr. intervals for 6 hrs. and as needed. Immediately following birth, the lamb received a 10 ml/kg transfusion with placental blood to support blood pressure and to allow for the blood sampling. The lamb was continuously monitored for temperature, hearth rate, and blood pressure.

The lamb was euthanized with IV pentobarbital at 6 hr. for tissue sampling.

A highly sensitive LC-MS assay of budesonide and hydrolysis procedure for analysis of budesonide esters is used. Tissues from other organs from the control lambs were used for baseline mRNA analyses. The 2018 groups of animals have blood drawn as follows for plasma levels of budesonide: 15 min, 30 min, 1 h, 2 h, 4 h, and 6 h. The animals sampled for tissue at 6 hr. will have budesonide measured on alveolar washes of the left lung and for residual budesonide in the left lung. Budesonide also was measured in other organs if indicated. We previously have measured budesonide levels only on plasma, lung, and BALF.

Plasma samples and betamethasone standards are extracted from sheep plasma, as follows: 20 μL of sample or standard was added to 50 μL of internal standard (budesonide-d8, 50 ng/mL) in a 10 mL glass test tube. Tubes are sealed, vortexed for 10 s and then incubated at room temperature for 5 min. 1 mL of ethyl acetate will then be added to each sample. Samples are vortexed for 2 min and then centrifuged (5 min, 3000 rpm, 24 degrees Celsius). 700 μL of supernatant was transferred to a glass 1.5 mL autosampler vial and dried under vacuum (30 minutes, 3000 rpm, 37 degrees Celsius). Samples are then re-suspended in 70 μL of a 1:1 methanol and water solution before being and incubated for 10 min, at 50° C., with gentle shaking.

Budesonide-exposed lung samples are extracted from as follows: 50 μL of internal standard (budesonide-d8, 50 ng/mL) was added to 100 mg of sample added in a 2 mL tissue maceration tube. 1 mL of ethyl acetate was then added to each sample. Samples were macerated using two cycles of 6,500 rpm×2 minutes. Samples are then incubated for 1 h at 50 degrees Celsius, centrifuged (5 min, 3000 rpm, 24 degrees Celsius) and filtered. 700 μL of cleared supernatant was transferred to a glass 1.5 mL auto-sampler vial and dried under vacuum (30 minutes, 3000 rpm, 37 degrees Celsius). Samples are then re-suspended in 70 μL of a 1:1 methanol and water solution before being and incubated (10 min at 50 degrees Celsius) with gentle shaking. Standards for lung analysis were extracted using an identical method, the only exception being that 50 μL of internal standard and 20 μL of plasma standard are added to 100 mg of fetal lung tissue collected from budesonide-naïve animals. Hydrolysis of lung tissue was performed with bovine pancreas cholesterol esterase dissolved in 0.1 M K$_2$HPO$_4$ buffer, pH 7.5, at a concentration of 0.0125 mg/ml with 10 mM taurocholate for 15 minutes prior to extraction.

The analysis is performed with Agilent Technologies 1290 Infinity pumps and a 6400 Series Triple Quadrupole LC/MS system, with an electrospray ionization source in positive ion mode. 20 μL of sample was injected in the MS and an Agilent Poroshell 2.1×50 mm C18, 2.6 uM column and a Phenomenex Biphenyl 3×150 mm, 2.6 uM column, are used to chromatographically separate analytes. The mobile phase for two-solvent gradient elution consisted of: (A1) Water+0.1% formic acid, and then (B1) Methanol+0.1% formic acid, delivered at a flow-rate of 0.5 mL/min, with a gradient of 50% B to 98% in 10 min, followed by re-equilibration for 2 min, prior to subsequent injection. The MS is set to detect precursor and product budesonide ions (acquisition time 3.9 minutes), with a mass of 431.5 and 323.0 respectively, and budesonide-d8 ions (acquisition time 3.83 minutes) with a mass of 439.5 and 421.5, respectively. Using a signal:noise ratio of 10:1 as a cut-off, budesonide concentrations can be reliably measured to concentrations as low as 0.01 ng/mL.

A pressure-volume curve for the lungs was measured for static lung compliance. The left lung was used for an alveolar wash and for measurements of residual budesonide. The right upper lobe was inflation fixed with formalin for histopathology and the right middle lobe was sampled for mRNA analysis. Brain, gut, and liver tissue was collected selectively for analysis of mRNA expression by mRNA-Seq to test if budesonide alters the expression of proteins for cell division, cell death, inflammation and early injury markers. This approach was more sensitive and definitive than measuring budesonide levels in tissue. The groups of animals are for analysis of lung inflammation and for assessments of budesonide effects on other organs.

This study evaluates the effects of lower doses of budesonide on mechanical ventilation induced lung and systemic injury. Based on previous results, the 6 hour time point was chosen for maximal effects on the budesonide on markers of injury and physiologic effects. Both injurious and non-injurious ventilation was used in the animals. Animals groups previously completed in 2017 were used for comparison with some overlapping groups. Physiologic variable and markers of injury was compared between the groups and previous years. Results are shown as means±SEM and reported as fold increase over controls, with control values set at 1. The Ventilation Efficiency Index (VEI) [3800/(PIP X rate X PaCO$_2$)] and Oxygenation Index (OI) [FiO$_2$ X Mean Airway Pressure)/PaO$_2$] were calculated (see Notter, R. H., et al., "Lung surfactant replacement in premature lambs with extracted lipids from bovine lung lavage: effects of dose, dispersion technique, and gestational age," Pediatr Res, 1985. 19 (6): p. 569-77 and Polglase, G. R., et al., "Lung and systemic inflammation in preterm lambs on continuous positive airway pressure or conventional ventilation," Pediatr Res, 2009. 65 (1): p. 67-71, both of which are incorporated herein by reference in their entireties). Statistics were analyzed using Prism 6 (GraphPad) by using Student's t-test, Mann-Whitney non-parametric, or ANOVA tests as appropriate. Significant was accepted as p<0.05.

Furthermore, messenger RNA (mRNA) was extracted from the peripheral lung tissue of the right middle lobe, and liver with TRIzol (Invitrogen). cDNA was produced from 1 μg mRNA using the Verso cDNA kit (Thermoscientific). Custom Taqman gene primers (Life Technologies) for ovine sequences for the epithelial sodium channel (ENaC), epiregulin (EREG), Interleukin 1B (IL-1B), IL-6, IL-8, monocyte chemoattractant protein-1 (MCP-1), serum amyloid A3 (SAA3), surfactant protein B (SFTPB), and TNF-α were used. Quantitative RT-PCR was performed with iTaq Universal mix (Bio-Rad) in a 15 μL reaction on a CFX Connect machine and software (Bio-Rad). 18S primers (Life Technologies) were used as the internal loading control.

Results

The mean airway pressure (MAP) and the volume at 40 cmH$_2$O (V40/kg) are reported in FIG. 2. Extrapolation of V40/Kg from the pressure-volume curve was performed according to a procedure known to the skilled person in the art.

Central to the pathogenesis of bronchopulmonary dysplasia (BPD) is the induction of a massive pulmonary inflammatory response due to postnatal mechanical ventilation and oxygen toxicity. The extent of the pro-inflammatory reaction and the disturbance of further alveolar growth and vasculogenesis can be indeed marked by pulmonary performance and ventilatory management in the first 24 hours.

In this regard, the volume at 40 cmH$_2$O from the pressure-volume curve at 6 hours, as a valuable integrated marker of lung injury (protein released into the lung or inflammation will cause edema and deactivate the surfactant triggering a vicious cycle where atelectasis, volotrauma, and high oxygen level exposure are promoted) constitutes an experimental acute proxy for the risk of BPD development.

The results show that the V40/kg was significantly higher in the budesonide 0.1 mg/kg and 0.04 mg/kg than in the surfactant only animals.

Furthermore, the animals receiving 0.25 mg/kg or 0.1 mg/kg had decreased mean airway pressure requirements. However, although there is a positive trend, said value did not reach significance variation for the group receiving 0.04 mg/kg.

Figure 3:
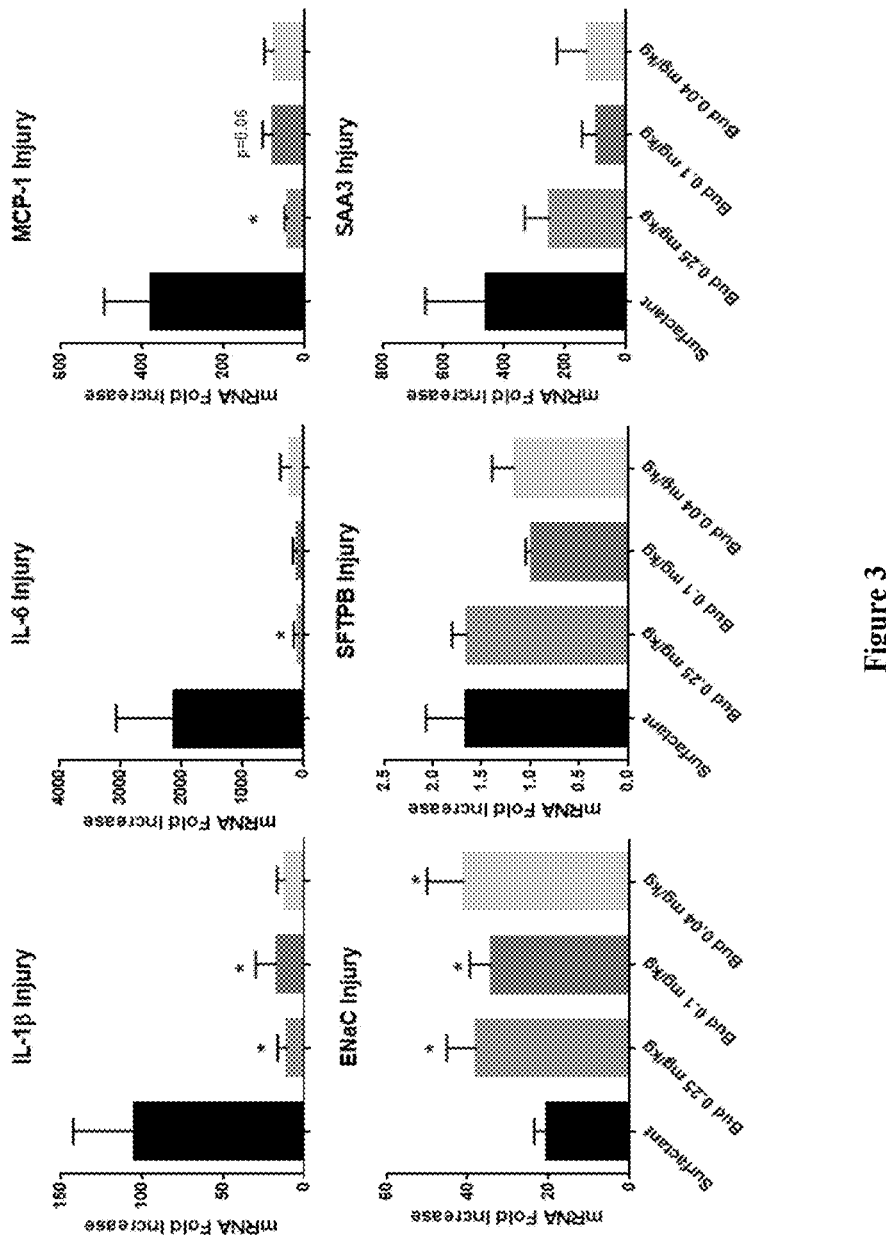
FIG. 3 shows the results of lung mRNA Evaluation for Injury of Example 6

The results of lung mRNA Evaluation for Injury are reported in FIG. 3. Injurious mechanical ventilation causes larger increases in mRNA for proinflammatory cytokines IL-1β, IL-6, and MCP-1 than with non-injurious ventilation (FIG. 6). Budesonide 0.25 mg/kg decreased mRNA for IL-1β, IL-6, and MCP-1. Budesonide 0.1 mg/kg decreased IL-6 mRNA and showed a strong trend to decrease MCP-1 (p=0.06). Although there were large variations in the responses, a slight trend to decrease was also observe for the 0.04 mg/kg dose.

ENaC mRNA further increased over surfactant only, which increased with mechanical ventilation, for all doses of budesonide. There were no changes in SFTPB or SAA3 compared with surfactant only animals in any dose.

Figure 4:
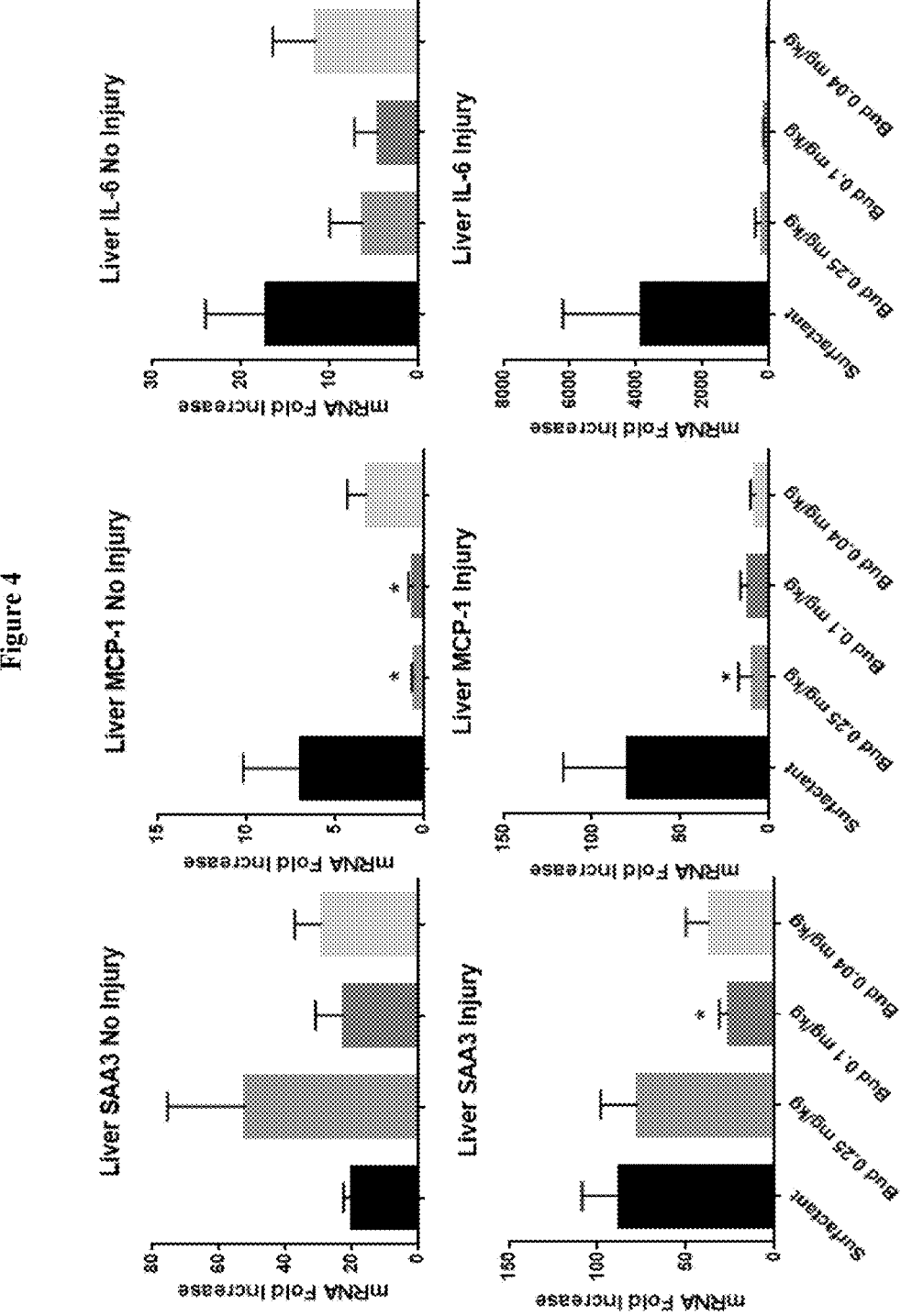
FIG. 4 shows the results of the Liver mRNA responses to mechanical ventilation of Example 6.

The results of the Liver mRNA responses to mechanical ventilation are reported in FIG. 4. Mechanical ventilation increased SAA3, MCP-1, and IL-6 mRNA in the liver. Large variations in the mRNA increases in the liver were found with non-injurious mechanical ventilation and injurious mechanical ventilation (FIG. 7). Budesonide 0.1 mg/kg decreased liver SAA3 mRNA. Budesonide 0.25 mg/kg and 0.1 mg/kg decreased liver MCP-1 mRNA with non-injurious ventilation, whereas only 0.25 mg/kg decreased MCP-1 with injury (due to the large variation in injured animals).

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the prophylaxis of bronchopulmonary dysplasia (BPD) in a preterm neonate, comprising administering to a preterm neonate poractant alfa in a dose of 200 mg/kg of body weight of said neonate and budesonide in a dose of 0.1 mg/kg of body weight of said neonate, wherein said poractant alfa and budesonide are administered from the 1$^{st}$ to the 4$^{th}$ day of life of the preterm neonate.

2. A method according to claim 1, wherein said preterm neonate is kept under a non-invasive ventilation procedure.

3. A method according to claim 2, wherein said non-invasive ventilation procedure is nasal CPAP.

4. A method according to claim 1, wherein said poractant alfa and budesonide are administered simultaneously.

5. A method according to claim 1, wherein said poractant alfa and budesonide are administered sequentially.

6. A method according to claim 1, wherein said poractant alfa and budesonide are administered separately.

7. A method according to claim 1, wherein said poractant alfa and budesonide are administered separately.

8. A method according to claim 1, wherein said poractant alfa and budesonide are administered in the form of an aqueous suspension comprising a pharmaceutically acceptable carrier.

9. A method according to claim 1, wherein said preterm neonate is of a gestational age of 26 to 35 weeks.

10. A method according to claim 1, wherein said preterm neonate is of a gestational age of 28 to 32 weeks.

11. A method according to claim 1, wherein:

said preterm neonate is kept under a non-invasive ventilation procedure;

said non-invasive ventilation procedure is nasal CPAP;

said preterm neonate is of a gestational age of 26 to 35 weeks; and said budesonide and said poractant alfa exhibit a synergistic effect.

12. A method according to claim 11, wherein said preterm neonate is of a gestational age of 28 to 32 weeks.

13. A method according to claim 11, wherein said poractant alfa and budesonide are administered simultaneously.

14. A method according to claim 11, wherein said poractant alfa and budesonide are administered sequentially.

15. A method according to claim 11, wherein said preterm neonate is of a gestational age of 28 to 32 weeks and said poractant alfa and budesonide are administered simultaneously.

16. A method according to claim 11, wherein said preterm neonate is of a gestational age of 28 to 32 weeks and said poractant alfa and budesonide are administered sequentially.

17. A method of reducing lung inflammation in a pre-term neonate treated with mechanical ventilation, comprising the step of administering a composition to said pre-term neonate, wherein said administration occurs during, before, or after said mechanical ventilation, and wherein the composition comprises:

(a) poractant alfa in a dose of 200 mg/kg of body weight of said neonate; in combination with (b) budesonide in a dose of 0.1 mg/kg of body weight of said neonate.

* * * * *